US011655464B2

(12) United States Patent
Lu et al.

(10) Patent No.: US 11,655,464 B2
(45) Date of Patent: May 23, 2023

(54) ALKALINE PROTEASE MUTANT, AND GENE, ENGINEERED STRAIN, PREPARATION METHOD AND APPLICATION THEREOF

(71) Applicants: Tianjin University of Science and Technology, Tianjin (CN); Shandong Lonct Enzymes Co. LTD, Linyi (CN)

(72) Inventors: Fuping Lu, Tianjin (CN); Yihan Liu, Tianjin (CN); Yu Li, Tianjin (CN); Xingji Wang, Linyi (CN); Kefen Wang, Linyi (CN); Wenlong Liu, Linyi (CN); Fufeng Liu, Tianjin (CN); Huitu Zhang, Tianjin (CN)

(73) Assignees: Tianjin University of Science and Technology, Tianjin (CN); Shandong Lonct Enzymes Co. LTD, Linyi (CN)

( * ) Notice: Subject to any disclaimer, the term of this patent is extended or adjusted under 35 U.S.C. 154(b) by 0 days.

(21) Appl. No.: 17/878,040

(22) Filed: Jul. 31, 2022

(65) Prior Publication Data
US 2023/0016224 A1  Jan. 19, 2023

Related U.S. Application Data

(63) Continuation of application No. PCT/CN2021/071281, filed on Jan. 12, 2021.

(30) Foreign Application Priority Data

Dec. 21, 2020  (CN) .......................... 202011513325.1

(51) Int. Cl.
| C12N 9/54 | (2006.01) |
| C12N 1/21 | (2006.01) |
| C12N 15/55 | (2006.01) |
| C12N 15/75 | (2006.01) |

(52) U.S. Cl.
CPC ...................... C12N 9/54 (2013.01)

(58) Field of Classification Search
None
See application file for complete search history.

(56) References Cited

U.S. PATENT DOCUMENTS

2014/0273177 A1* 9/2014 Basler ................ C12N 9/64
                                                    435/264
2015/0125925 A1* 5/2015 Souter ................ C11D 3/38681
                                                    435/197

FOREIGN PATENT DOCUMENTS

| CN | 1537163 A | 10/2004 |
| CN | 1757721 A | 4/2006 |
| CN | 105176951 A | 12/2015 |
| CN | 106661566 A | 5/2017 |
| CN | 107384897 A | 11/2017 |
| CN | 110283880 A | 9/2019 |
| CN | 110819612 A | 2/2020 |
| CN | 111334494 A | 6/2020 |
| CN | 112458072 A | 3/2021 |

OTHER PUBLICATIONS

Cuixia Zhou, et al., Development and application of a CRISPR/Cas9 system for Bacillus licheniformis genome editing. International Journal of Biological Macromolecules, 2019, pp. 329-337, vol. 122.
FJ940727.1, Bacillus alcalophilus strain TCCC11004 alkaline protease gene, complete cds, GenBank, 2009, pp. 1-2.

* cited by examiner

*Primary Examiner* — Robert B Mondesi
*Assistant Examiner* — Todd M Epstein
(74) *Attorney, Agent, or Firm* — Bayramoglu Law Offices LLC

(57) ABSTRACT

An alkaline protease mutant, and a gene, engineered strain, a preparation method and application thereof are provided. The method comprises the following steps of extracting genome DNA of *Bacillus clausii*, performing PCR amplification to obtain a wild-type alkaline protease gene sequence, mutating the wild-type alkaline protease gene obtained by the amplification through an error-prone PCR, performing high-throughput screening to obtain a plurality of highly active alkaline protease genes, performing DNA shuffling on the highly active alkaline protease genes, and performing screening to obtain eight alkaline protease mutant genes with higher activity.

9 Claims, 4 Drawing Sheets

Specification includes a Sequence Listing.

ALKALINE PROTEASE MUTANT, AND GENE, ENGINEERED STRAIN, PREPARATION METHOD AND APPLICATION THEREOF

CROSS REFERENCE TO RELATED APPLICATIONS

This application is a continuation application of International Application No. PCT/CN2021/071281, filed on Jan. 12, 2021, which is based upon and claims priority to Chinese Patent Application No. 202011513325.1, filed on Dec. 21, 2020, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBRSMJ034-Sequence_Listing.xml, created on Aug. 18, 2022, and is 27,938 bytes in size.

TECHNICAL FIELD

The present disclosure belongs to the technical field of bioengineering and particularly relates to an alkaline protease mutant, and a gene, engineered strain, a preparation method and application thereof.

BACKGROUND

Protease, a hydrolase, can degrade protein molecules and polypeptides into small peptide chains and amino acids by catalyzing splitting of protein peptide bonds. The protease can be divided into a neutral protease, an acid protease and an alkaline protease according to different suitable pH values of the protease during the action. The alkaline protease has an optimum reaction pH value generally more than 9 and has a stronger enzyme activity, a heat resistance, an alkali resistance and an esterase characteristic compared with other proteases. Due to these advantages, the alkaline protease is more widely used in industry and has a very important function in the industries of detergent, food processing, feed, environmental protection, leather manufacturing and silk manufacturing. When the alkaline protease is added into the detergent, the detergent can keep an original color of washed clothes, improves a decontamination effect of a product, effectively reduces dosage of a surfactant and certain auxiliaries in the detergent, and can also save water and energy, and protects the environment. The alkaline protease is mainly used for hydrolyzing plant proteins in food and the plant protein is converted into peptides and amino acids with smaller molecular weight after hydrolysis, such that the product is more easily digested and absorbed, and has higher nutritional value and better quality and safety of the product. In a leather-manufacturing process, skins and furs containing proteins and protein analogues as main components are generally difficult to treat. A traditional method utilizes toxic chemical substances for the treatment. But the method harms safety of people and also causes great pollution to the environment. The protease can replace the chemical substances to degrade non-colloid components and non-fibrous protein in the leather-manufacturing process, and meanwhile can further reduce the pollution to the environment.

Microorganisms are an important origin of the protease, compared with plant protease and animal protease, microorganisms can produce a large amount of enzymes meeting a production requirement since the microorganisms are rapid to grow and easy for artificial genetic modification, capable of producing a rich protease resource and can be cultured in a large amount in a relatively short time. The alkaline protease-producing microorganisms are mainly separated from alkaline environments such as saline and alkaline lakes, deep sea, sandy lands and the like. Currently, *Bacillus*, *Actinomycetes* and fungi are reported to produce the alkaline protease, but the *Bacillus* is the one which is mainly used in industrial production. However, since the strain has a limited enzyme-producing capacity, an activity of a fermentation enzyme is not high. The alkaline protease produced by the *Bacillus* has a relatively high cost, such that a large-scale application of the *Bacillus* is limited. Therefore, it is of important significance to improve the activity of the alkaline protease in industrial production and application.

Protein engineering is a new technology established on the basis of genetic engineering and mainly depends on the auxiliary design of computer software and basic knowledge of multidisciplinary such as protein chemistry. The protein engineering can obtain novel proteins meeting requirements of human by artificially directionally modifying protein-coding genes and modifying, remodeling, and splicing proteins. A directed evolution of enzymes, also known as an in-vitro molecular directed evolution of enzymes, belongs to an irrational design of proteins and thus is a new development direction of protein engineering. Special evolutionary conditions are artificially created by stimulating a natural evolutionary process without knowing structures, active sites, catalytic mechanism and other factors of proteins in advance. Starting from one or more existing parent enzymes (naturally or artificially obtained enzyme precursors), random mutation of genes in vitro or in vivo or in-vitro gene recombination are performed to construct an artificial mutant enzyme library, and evolutionary enzymes with certain characteristics expected in advance are finally obtained through certain screening or selection methods.

Error-prone PCR and DNA shuffling are commonly used methods for the in-vitro directed evolution. The error-prone PCR, a method for inducing DNA sequence variation in vitro, is to reduce fidelity of DNA replication by using a low-fidelity TaqDNA polymerase and changing PCR reaction conditions, such as adding Mn, changing the number of cycles and dNTP concentration, etc., increase base mispairing during synthesis of new DNA strands, and thus enable an amplified product to have more point mutations.

DNA shuffling is to cut one or a group of closely related gene sequences into a series of small DNA fragments of random sizes under the action of DNaseI. Due to homology of genes, some of base sequences overlap between these small fragments. A full-length gene is generated by self-guide and random recombination of the small fragments and PCR of specific primers. In this process, an exchange of related sequences occurs due to a transformation of templates, thus a variety of gene recombination libraries are generated. Products of shuffled gene expression are further screened to achieve the directed evolution of a target gene.

SUMMARY

The present disclosure provides an alkaline protease mutant, and a gene, engineered strain, a preparation method and application thereof, and specifically provides a alkaline protease mutant with high activity, and a gene and engineered strain thereof.

In the present disclosure, a *Bacillus* expression system has the following advantages: 1. *Bacillus* has a system of efficient secretion signal peptides and molecular chaperones, and thus is conducive to an efficient expression of a target protein; 2. most *Bacillus* is non-pathogenic and in line with general safety requirements in industrial production; 3. a cell wall composition of the *Bacillus* is relatively simple, which is conducive to extracellular secretion of expressed proteins and downstream recovery and purification of proteins, and will not lead to accumulation of secreted proteins in cells; and 4. as a single-celled organism, *Bacillus* can achieve a high cell density in a short time, requires a relatively simple medium composition, has a relatively low cost and meets requirements of industrial production.

In the present disclosure, based on an alkaline protease expression platform of *Bacillus subtilis*, error-prone PCR and DNA shuffling are utilized to carry out molecular modification on an alkaline protease gene from *Bacillus clausii* to obtain an alkaline protease gene with high activity, and which is also successfully expressed in systems of *Bacillus amyloliquefaciens*, *Bacillus licheniformis* and *Bacillus clausii*.

One of the technical solutions provided by the present disclosure is as follows: cloning a wild alkaline protease zymogen region gene apr (shown in SEQ ID NO: 3) sequence (an amino acid sequence as shown in SEQ ID NO: 4) by taking a genome of *Bacillus clausii* CGMCC NO. 12953 as a template, randomly mutating the wild alkaline protease gene by continuous error-prone PCR, performing high-throughput screening using a *Bacillus subtilis* expression system to obtain a plurality of highly active alkaline protease mutant genes, performing DNA shuffling on the highly active alkaline protease mutant genes, and screening to obtain the highly active alkaline protease mutant genes.

Another one of the technical solutions provided by the present disclosure is as follows: constructing recombinant vectors of the mutant genes, successfully expressing the mutant genes in *Bacillus amyloliquefaciens*, *Bacillus licheniformis* and *Bacillus clausii* to obtain recombinant strains with an improved enzyme-producing activity, and a novel alkaline protease is further obtained by optimizing a fermentation process and can be used in the fields of detergents, food, tanning, medicines and the like.

The following definitions are used in the present disclosure:

1. Nomenclature for Amino Acid and DNA Nucleic Acid Sequences

An accepted IUPAC nomenclature is used for amino acid residues in a form of a three letter code. An accepted IUPAC nomenclature is used for DNA nucleic acid sequences.

2. Identification of Highly Active Alkaline Protease Mutant

"the original amino acid residue and the location number and the mutant amino acid residue" is used to indicate a mutated amino acid residue in a highly active alkaline protease mutant. In the present disclosure, mutation point positions are numbered according to an amino acid sequence of a mature peptide of the alkaline protease. The position number corresponds to the amino acid sequence of the mature peptide of the wild-type alkaline protease in SEQ ID NO: 6. For example, Asn212 represents that a 212nd amino acid residue of the amino acid sequence of the mature peptide of the wild-type alkaline protease is Asn. Asn212Ser represents that the 212nd amino acid residue is changed from Asn of the wild-type alkaline protease to Ser and can also be represented by a single letter abbreviation of the amino acid, such as N212S. The amino acid sequence with multi-site mutation is represented using "/" to connect each mutation simultaneously, for example, V11I/G95V/V145I/N212S represents the amino acids residue at positions 11, 95, 145, and 212 are sequentially replaced as follows: V of the wild-type alkaline protease is replaced by I, G is replaced by V, V is replaced by I, and N is replaced by S. Representation of the nucleotides is similar to that of the amino acids. The position number corresponds to a nucleotide sequence of the wild-type alkaline protease in SEQ ID NO: 5, such as C425, indicating that a base at position 425 of the nucleotide sequence of the alkaline protease is C.

In the present disclosure, APR represents wild-type alkaline protease, namely an original sequence shown in SEQ ID NO: 4 and a coding gene is shown as apr (shown in SEQ ID NO: 3). Each alkaline protease mutant is represented by APRM plus the number X and a gene encoding each mutant is shown in lowercase italics in its amino acid representation.

In the present disclosure, the alkaline protease mutant has a proteolytic activity and a mature peptide is as follows:

(1) obtained by generating any one of the following mutation based on a mature peptide of a wild-type alkaline protease shown in SEQ ID NO: 6:

V11I/G23A/G25P/I35V/G95P/S99H/V145I/N212S/A267G,

V11L/G23A/G25P/I35V/G95P/S99H/V145I/N212S/A267G,

V11L/G23A/G25A/I35V/G95P/S99H/V145I/N212S/A267G,

V11I/G23A/G25A/I35V/G95P/S99H/V145I/N212S/A267G,

V11I/G23A/G25A/I35V/G95P/S99H/V145I/N212S/A267P,

V11L/G23A/G25A/I35V/G95P/S99H/V145I/N212S/A267P,

V11I/G23A/G25P/I35V/G95P/S99H/V145I/N212S/A267P, or

V11L/G23A/G25P/I35V/G95P/S99H/V145I/N212S/A267P; or (2) an amino acid sequence with more than 75% homology to (1); or (3) an amino acid sequence with a same function as (1) obtained after one or more amino acid residue substitutions, and/or deletions, and/or additions based on (1).

Error-prone PCR and DNA shuffling are used to mutate a wild-type alkaline protease gene and eight highly active alkaline protease mutants are obtained by screening.

The present disclosure further provides an encoding gene of the mutant.

In some examples, the encoding gene of the mutant is shown in any one of SEQ ID NOS: 7-14.

The present disclosure further provides a recombinant vector or a recombinant strain comprising the mutant or its encoding gene.

In some examples, the recombinant vector has an expression vector of pBSA43.

In some examples, a host cell expressing the encoding gene of the mutant is *Bacillus subtilis*, *Bacillus amyloliquefaciens*, *Bacillus licheniformis*, or *Bacillus clausii*.

The highly active alkaline protease mutant gene of the present disclosure is expressed in expression systems of *Bacillus subtilis*, *Bacillus amyloliquefaciens*, *Bacillus licheniformis*, and *Bacillus clausii* and highly active alkaline protease powder is obtained by purification.

In some examples, the *Bacillus subtilis* is WB600.

In some examples, the *Bacillus amyloliquefaciens* has an accession number of CGMCC No. 11218.

In some examples, the *Bacillus licheniformis* is TCCC11965.

In some examples, the *Bacillus clausii* has an accession number of CGMCC No. 12953.

pBSA43 is obtained by using an *Escherichia coli-Bacillus* shuttle cloning vector pBE2 as a backbone and cloning into a strong *Bacillus* constitutive promoter P43 and a signal sequence sacB of levansucrase capable of directly secreting a recombinant protein into a medium. The pBSA43 carries an Amp$^r$ gene which can be used as a selection marker for ampicillin resistance in *Escherichia coli* and also carries a Km$^r$ gene which can be used as a selection marker for kanamycin resistance in *Bacillus subtilis* and *Bacillus licheniformis*.

Specific experimental steps of the present disclosure are as follows:

(1) randomly mutating an alkaline protease gene from *Bacillus clausii* by error-prone PCR to obtain a randomly mutated gene aprmx$_1$, ligating the gene to an expression vector and transforming the recombinant vector into *Bacillus subtilis* WB600 for screening, performing error-prone PCR again using an highly active mutant gene as a template, repeating three times, and thus obtaining a plurality of highly active alkaline protease mutant genes;

(2) performing DNA shuffling on the highly active mutant genes screened by the error-prone PCR, ligating the shuffled mutant gene aprmx$_2$ to the expression vector and transforming the recombinant vector into *Bacillus subtilis*, and thus obtaining eight highly active alkaline protease mutant genes through high-throughput screening;

(3) ligating the obtained highly active alkaline protease mutant genes into the expression vector and transforming the recombinant vector into *Bacillus amyloliquefaciens*, *Bacillus licheniformis* and *Bacillus clausii* to obtain each recombinant strain; and (4) expressing the recombinant strain and thus obtaining the highly active alkaline protease mutant APRMX after purification.

Beneficial Effects:
1. Error-prone PCR and DNA shuffling are used to mutate a wild-type alkaline protease gene and eight highly active alkaline protease mutants are obtained by screening.
2. The highly active alkaline protease mutant gene of the present disclosure is expressed in expression systems of *Bacillus subtilis*, *Bacillus amyloliquefaciens*, *Bacillus licheniformis*, and *Bacillus clausii* and highly active alkaline protease powder is obtained by purification.

BRIEF DESCRIPTION OF THE DRAWINGS

FIG. 6A is an optimal reaction temperature curve of the wild-type alkaline protease APR;
FIG. 6B is an optimal reaction pH of the wild-type alkaline protease APR;
FIG. 6C is a temperature stability curve of the wild-type alkaline protease APR at 60° C.;
and
FIG. 6D is a pH stability curve of the wild-type alkaline protease APR at a pH of 11.

DETAILED DESCRIPTION OF THE EMBODIMENTS

Figure 1:
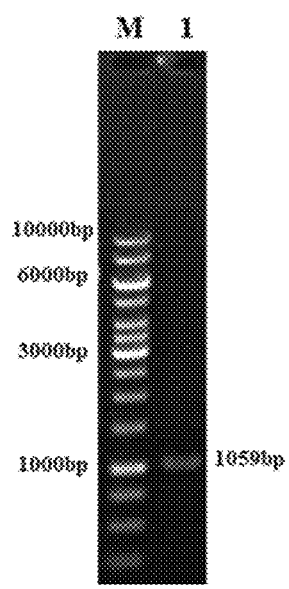
FIG. 1 is an electrophoresis diagram of PCR amplification of a wild-type alkaline protease zymogen gene in an example of the present disclosure,
where, M is DNA Marker and 1 is an alkaline protease zymogen gene apr.

To make the objective, technical solutions and advantages of the patent clearer and more comprehensible, the present patent will be further described below in detail in conjunction with specifically examples. It should be understood that the specific examples described herein are merely intended to explain the patent, rather than to limit the present disclosure.

The *Bacillus licheniformis* used in the present disclosure is TCCC11965, disclosed in Development and application of a CRISPR/Cas9 system for *Bacillus licheniformis* genome editing [J]. International Journal of Biological Macromolecules, 2019, 122: 329-337, and currently deposited in Microbial Culture Collection and Management Center of Tianjin University of Science and Technology, and the public can inquire and obtain the strain from the Center.

EXAMPLE 1

Acquisition of Wild-type Alkaline Protease Gene

1. A wild-type alkaline protease gene was from a *Bacillus clausii* CGMCC NO. 12953 strain preserved in the laboratory. Its genomic DNA was extracted by a kit (OMEGA: Bacterial DNA Kit). The genomic DNA of the *Bacillus clausii* was extracted by the following steps:

(1) strain activation: a little bacterial solution was dipped from a glycerol tube with an inoculation loop and inoculated on an LB solid medium plate in a manner of drawing lines to form three zones, and the bacteria were cultured at 37° C. for 12 h;

(2) strain culturing: single colonies were picked from a plate for culturing bacteria and inoculated into 5 mL of a liquid LB medium, and the bacteria were cultured with shaking at 220 rpm and 37° C. for 12 h;

(3) collection of bacteria: an appropriate amount of a cultured bacterial solution was sub-packaged into sterilized 1.5-mL EP tubes, the bacterial solution was centrifuged at 12,000 rpm for 1 min to collect the bacteria, and a supernatant was discarded;

(4) 100 μL of ddH$_2$O was added to resuspend the bacteria, 50 μL of 50 mg/mL of lysozyme was added, and water bath was performed at 37° C. for 10 min;

(5) 100 μL of a BTL Buffer and 20 μL of a proteinase K were added, an obtained mixture was vortex-shaken, subjected to water bath at 55° C. for 40-50 min, and shaken and uniformly mixed every other 20-30 min;

(6) 5 μL of RNase was added, and an obtained mixture was uniformly mixed several times in an inverted manner and placed at a room temperature for 5 min;

(7) the obtained mixture was centrifuged at 12,000 rpm for 2 min, an undigested part was removed, a supernatant part was transferred to a new 1.5-mL EP tube, 220 μL of a BDL Buffer was added, and an obtained mixture was shaken and uniformly mixed, and subjected to water bath at 65° C. for 10 min;

(8) 220 μL of absolute ethanol was added and an obtained mixture was pipetted and uniformly mixed;

(9) liquid in the EP tube was transferred to an adsorption column for standing for 2 min and centrifuged at 12,000 rpm for 1 min, a filtrate was poured back into the adsorption column for standing and centrifugation, the operation was repeated twice, and a filtrate was discarded;

(10) 500 μL of a HBC Buffer was added, an obtained mixture stood for 2 min and centrifuged at 12,000 rpm for 1 min, and a filtrate was discarded;

(11) 700 μL of a DNA Wash Buffer was added, an obtained mixture stood for 2 min and centrifuged at 12,000 rpm for 1 min, and a filtrate was discarded;

(12) 500 μL of a DNA Wash Buffer was added, an obtained mixture stood for 2 min and centrifuged at 12,000 rpm for 1 min, and a filtrate was discarded;

(13) centrifugation was performed at 12,000 rpm for 2 min, and the adsorption column was put in a new EP tube, placed in a metal bath at 55° C. for 10 min, and air-dried; and

(14) 50 μL of molecular water at 55° C. was added, and an obtained mixture stood at a room temperature for 3-5 min and was centrifuged at 12,000 rpm for 2 min to collect a genome.

2. The extracted genome of the *Bacillus clausii* was used as a template, a pair of primers was designed at an upstream and a downstream of an ORF according to an alkaline protease sequence registered with a Genbank serial number of FJ940727.1, and restriction sites of BamHI and HindIII were introduced separately. The alkaline protease gene of the present disclosure has amplification primers as follows:

```
upstream primer P1 (SEQ ID NO: 1):
5'-CGCGGATCCGCTGAAGAAGCAAAAGAAAAATATTTAAT-3';
and downstream primer P2 (SEQ ID NO: 2):
5'-CCCAAGCTTTTAGCGTGTTGCCGCTTCT-3'.
```

P1 and P2 were used as the upstream and downstream primer separately, and the alkaline protease genome of the *Bacillus clausii* was used as a template for amplification.

A reaction system for the amplification was as follows:

| | |
|---|---|
| 10 × PCR Buffer | 5.0 μL |
| dNTPs | 5.0 μL |
| Upstream primer P1 | 2.0 μL |
| Downstream primer P2 | 2.0 μL |
| DNA template | 2.0 μL |
| Pyrobest enzyme | 0.5 μL |
| ddH$_2$O | 33.5 μL |

Figure 2:
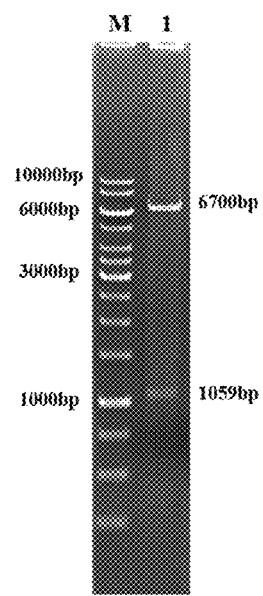
FIG. 2 is a verification diagram of digestion of a pBAS43-apr plasmid in an example of the present disclosure,
where, M is DNA Marker and 1 is a double digestion map of pBSA43-apr by BamHI and HindIII.

An amplification process was as follows: pre-denaturation at 95° C. for 10 min; denaturation at 94° C. for 30 s, annealing at 57° C. for 45 s, and extension at 72° C. for 1 min 20 s, a total of 30 cycles; and extension at 72° C. for 10 min. A PCR amplified product was subjected to 0.8% agarose gel electrophoresis to obtain a band of 1,059 bp (FIG. 1). The PCR product was recovered with a small DNA recovery kit to obtain the wild-type alkaline protein gene apr (SEQ ID NO: 3), the amplified apr was ligated with a vector pBSA43 to obtain a recombinant plasmid pBSA43-apr, a digestion verification was shown in FIG. 2, and the recombinant plasmid was transformed into *Escherichia coli* JM109 and *Bacillus subtilis* WB600.

EXAMPLE 2

Screening of Highly Active Alkaline Protease Mutants by Construction of Alkaline Protease Mutant Library by Error-prone PCR 1. Random mutation was performed based on error-prone PCR to construct an alkaline protease mutant library. Primers were designed as follows:

```
upstream primer P1 (SEQ ID NO: 1):
5'-CGCGGATCCGCTGAAGAAGCAAAAGAAAAATATTTAAT-3';
and downstream primer P2 (SEQ ID NO: 2):
5'-CCCAAGCTTTTAGCGTGTTGCCGCTTCT-3'.
```

In an error-prone PCR reaction system, P1 and P2 were used as the upstream and downstream primer separately, a wild-type alkaline protease gene apr was used as a template, and error-prone PCR was performed.

A reaction system for an amplification was as follows:

| | |
|---|---|
| 10 × PCR Buffer (free of Mg$^{2+}$) | 5 μL |
| dATP | 0.1 μL |
| dGTP | 0.1 μL |
| dCTP | 0.5 μL |
| dTTP | 0.5 μL |
| Upstream primer P1 | 2 μL |
| Downstream primer P2 | 2 μL |
| Wild-type alkaline protease gene | 2 μL |
| rTaq DNA polymerase | 0.3 μL |
| 25 mM MgCl$_2$ (10 mM) | 20 μL |
| 5 mM MnCl$_2$ (0.3 mM) | 3 μL |
| ddH$_2$O | 14.5 μL |

Figure 3:
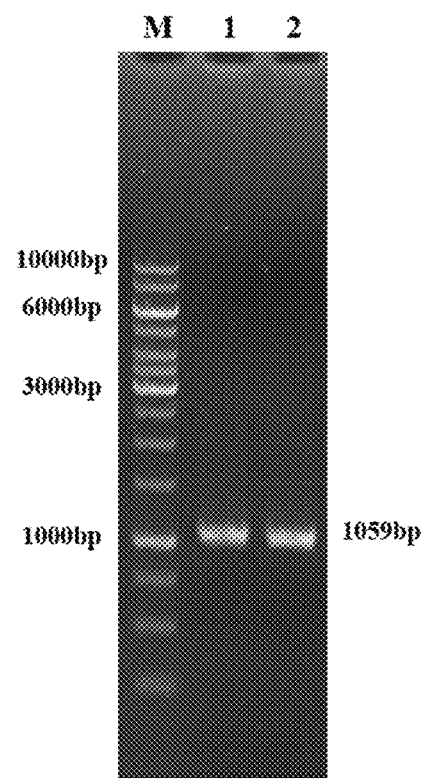
FIG. 3 is an electrophoresis diagram of error-prone PCR amplification of an alkaline protease mutant gene in an example of the present disclosure,
where, M is DNA Marker and 1 and 2 show an electrophoresis diagram of error-prone PCR amplification of an alkaline protease mutant gene aprmx$_1$.

An amplification process was as follows: pre-denaturation at 95° C. for 10 min; denaturation at 98° C. for 10 s, annealing at 57° C. for 30 s, and extension at 72° C. for 1 min 20 s, a total of 30 cycles; and extension at 72° C. for 10 min. A PCR amplified product was subjected to 0.8% agarose gel electrophoresis (FIG. 3). The PCR product was recovered with a small DNA recovery kit to obtain an alkaline protease gene aprmx$_i$ with random mutation (x$_1$ represents several different randomly mutated genes).

2. The alkaline protease random mutant gene aprmx$_1$ was ligated with a vector pBSA43 to transform into JM109, the plasmid was extracted to obtain a recombinant plasmid pBSA43-aprmx$_1$, the recombinant plasmid pBSA43-aprmx$_1$ was transformed into *Bacillus subtilis* WB600, transformants were picked into a 48-well plate containing 500 μL of an LB liquid medium, the 48-well plate was placed in a 48-well plate shaker and cultured at 37° C. and 750 r/min for 48 h, a supernatant was taken after the culture to obtain a crude alkaline protease solution, activity of the alkaline protease was determined by a short peptide substrate method, and the transformants with higher enzyme activity than a wild type were picked out. The recombinant plasmids extracted from transformant with high enzyme activity were used as templates, continuous error-prone PCR was performed, screening was performed according to the above method, the operation was repeated for three times, several mutant strains with high alkaline protease activity were finally screened, and the alkaline protease mutant plasmids with high activity were used as templates for DNA shuffling.

3. Determination of alkaline protease activity with short peptide substrates

Short peptide substrates: N-Succinyl-Ala-Ala-Pro-Phe-p-nitroanilide (AAPF, represented by single letter abbreviation of amino acids, similarly hereinafter), AAPY, AAPW, AAPA, AAPR, AAPN, AAPD, AAPC, AAPQ, AAPE, AAPG, AAPH, AAPI, AAPL, AAPK, AAPM, AAPP, AAPS, AAPT and AAPV were mixed and dissolved in dimethyl sulfoxide (DMSO), such that each substrate had a concentration of 6 mmol/L (a method refers to the patent "New method for measuring activity of protease" with an application number of 201910730238.2).

Determination method: 80 μL of a boric acid buffer at a pH of 10.5 and 20 μL of a short peptide substrate solution were added to a 96-well plate, and incubated in a 40° C. water bath kettle for 1 min, 100 μL of a diluted enzyme solution (100 μL of a boric acid buffer at a pH of 10.5 was added to a negative control) was added, reaction was performed at 40° C. for 10 min, and absorbance was measured at 410 nm with a microplate reader. One unit (U) of enzyme activity was defined as that 1 mL of an enzyme solution hydrolyzes a substrate for 1 min to produce 1 μmol of p-nitroaniline under the above condition.

EXAMPLE 3

Screening of Highly Active Alkaline Protease Mutants by Construction of Alkaline Protease Mutant Library by DNA Shuffling The alkaline protease mutant genes obtained by the screening by the error-prone PCR in example 2 were subjected to DNA shuffling and highly active alkaline protease mutants were obtained by high-throughput screening.

1. Fragmentation of Alkaline Protease Mutant Genes

The recombinant plasmids of the alkaline protease mutant strains obtained by the screening by the error-prone PCR were extracted, the recombinant plasmids were digested with restriction enzymes BamHI and HindIII, DNA fragments of the alkaline protease mutant genes were recovered by Gel Extraction, the DNA fragments of the mutant genes were uniformly mixed in an equal amount, 1 μg of the mixed DNA fragments were added to 100 μL of a buffer system (50 mmol/L Tris-HCl at a pH of 7.4 and 1 mmol/L MgCl$_2$), DNaseI at a final concentration of 0.01 U was added, enzyme digestion was performed at 37° C. for 20 min, and enzyme inactivation was performed at 90° C. for 10 min. A digested product was subjected to 2% agarose gel electrophoresis and fragments of about 50-200 bp were recovered with a small DNA recovery kit.

2. Primerless PCR

The small fragments recovered after the above digestion were used as templates and primerless PCR was performed using the small fragments as primers for each other. A reaction system for an amplification was as follows:

| | |
|---|---|
| 10 × PCR Buffer (free of Mg$^{2+}$) | 5.0 μL |
| 25 mM MgCl$_2$ | 5.0 μL |
| dNTPs | 5.0 μL |
| DNA fragment templates | 2.0 μL |
| rTaq DNA polymerase | 0.5 μL |
| ddH$_2$O | 37.5 μL |

An amplification process was as follows: pre-denaturation at 95° C. for 10 min; denaturation at 98° C. for 10 s, annealing at 50° C. for 30 s, and extension at 72° C. for 1 min 20 s, a total of 30 cycles; and extension at 72° C. for 10 min. A PCR amplified product was subjected to 0.8% agarose gel electrophoresis and a DNA fragment of about 1 kb was recovered with a small DNA recovery kit.

2. PCR With Primers

The primerless PCR product was used as a template to be subjected to a second round of PCR with primers, and the amplification primers were as follows:

```
upstream primer P1 (SEQ ID NO: 1):
5'-CGCGGATCCGCTGAAGAAGCAAAAGAAAAATATTTAAT-3';
and downstream primer P2 (SEQ ID NO: 2):
5'-CCCAAGCTTTTAGCGTGTTGCCGCTTCT-3'.
```

A reaction system for an amplification was as follows:

| | |
|---|---|
| 10 × PCR Buffer | 5.0 μL |
| dNTPs | 5.0 μL |
| Upstream primer P1 | 2.0 μL |
| Downstream primer P2 | 2.0 μL |
| Primerless PCR product | 2.0 μL |
| Pyrobest enzyme | 0.5 μL |
| ddH$_2$O | 33.5 μL |

Figure 4:
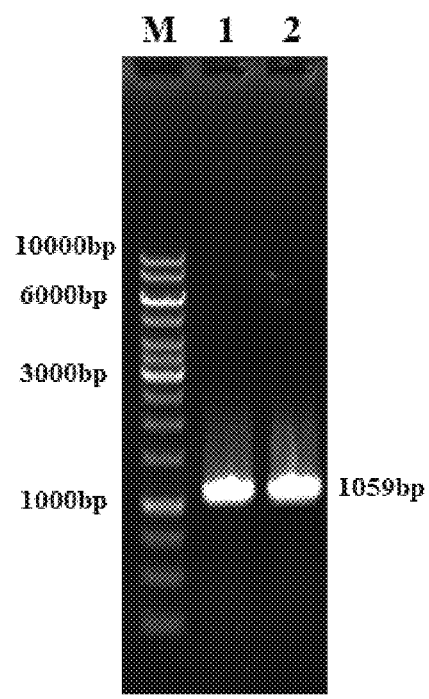
FIG. 4 is an electrophoresis diagram of a product of DNA shuffling of an alkaline protease mutant gene in an example of the present disclosure,
where, M is DNA Marker and 1 and 2 show an electrophoresis diagram of a shuffled gene aprmx$_2$ of an alkaline protease mutant.

An amplification process was as follows: pre-denaturation at 95° C. for 10 min; denaturation at 94° C. for 30 s, annealing at 57° C. for 45 s, and extension at 72° C. for 1 min 20 s, a total of 30 cycles; and extension at 72° C. for 10 min. A PCR amplified product was subjected to 0.8% agarose gel electrophoresis (FIG. 4). A DNA fragment of about 1 kb was recovered with a small DNA recovery kit to obtain alkaline protease shuffled genes aprmx$_2$ (x$_2$ represents several different shuffled genes).

4. The alkaline protease shuffled genes aprmx$_2$ were separately cloned into an expression vector pBSA43 to obtain several recombinant plasmids pBSA43-aprmx$_2$ to be transformed into JM109, extraction was performed to obtain the recombinant plasmids pBSA43-aprmx$_2$, the recombinant plasmids pBSA43-aprmx$_2$ were transformed into *Bacillus subtilis* WB600, transformants were picked into a 48-well plate containing 500 μL of an LB liquid medium, the 48-well plate was placed in a 48-well plate shaker and cultured at 37° C. and 750 r/min for 48 h, a supernatant was taken after the culture to obtain a crude alkaline protease solution, activity of the alkaline protease was determined by a short peptide substrate method in example 2, and the transformants with higher enzyme activity than a wild type were picked out. After screening, eight mutant strains WB600/pBSA43-aprmX (X are 1-8 separately and aprmX represents 8 different mutant encoding genes specifically as shown in Table 1) with higher alkaline protease activity were obtained. Plasmids of the obtained highly active alkaline protease mutant strains were extracted and sequenced (Beijing Huada Bioengineering Company). The results showed the obtained 8 highly active alkaline protease mutants in the following table.

TABLE 1

Information of alkaline protease mutants

| Mutants | Mutated amino acids residue | Gene Name | SEQ ID NO: |
|---|---|---|---|
| APR | V11/G23/G25/I35/G95/S99/V145/N212/A267 | apr | 3 |
| APRM 1 | V11I/G23A/G25P/I35V/G95P/S99H/V145I/N212S/A267G | aprm1 | 7 |
| APRM 2 | V11L/G23A/G25P/I35V/G95P/S99H/V145I/N212S/A267G | aprm2 | 8 |
| APRM 3 | V11L/G23A/G25A/I35V/G95P/S99H/V145I/N212S/A267G | aprm3 | 9 |
| APRM 4 | V11I/G23A/G25A/I35V/G95P/S99H/V145I/N212S/A267G | aprm4 | 10 |
| APRM 5 | V11I/G23A/G25A/I35V/G95P/S99H/V145I/N212S/A267P | aprm5 | 11 |
| APRM 6 | V11L/G23A/G25A/I35V/G95P/S99H/V145I/N212S/A267P | aprm6 | 12 |
| APRM 7 | V11I/G23A/G25P/I35V/G95P/S99H/V145I/N212S/A267P | aprm7 | 13 |
| APRM 8 | V11L/G23A/G25P/I35V/G95P/S99H/V145I/N212S/A267P | aprm8 | 14 |

EXAMPLE 4

Determination of Specific Activity of Highly Active Alkaline Protease Mutants

The mutant recombinant strains WB600/pBSA43-aprmX (X is 1, 2, 3, 4, 5, 6, 7, and 8, similarly hereinafter) obtained in step 4 of example 3 and a wild-type recombinant strain WB600/pBSA43-apr were inoculated in 5 mL of a LB liquid medium (containing 50 µg/mL of kanamycin) separately and cultured at 37° C. and 220 r/min overnight, the cultured strains were transferred to 50 mL of a fresh LB medium (containing 50 µg/mL of kanamycin) at an inoculum size of 2%, and the strains were continuously cultured at 37° C. and 220 r/min for 48 h.

A fermentation broth was centrifuged, a supernatant was taken, impure proteins were removed by salting out with ammonium sulfate at a saturation of 25%, and the saturation was increased to 65% to precipitate a target protein. After the precipitate was dissolved, dialysis was performed to remove salt, an active component obtained after salting out to desalt was dissolved with 0.02 mol/L of a Tris-HCl (pH 7.0) buffer, an obtained sample was loaded on a cellulose ion exchange chromatography column, unadsorbed protein was first eluted using the same buffer, and a target protein was collected by gradient elution with 0.02 mol/L of a Tris-HCl (pH 7.0) buffer containing different concentrations of NaCl (0-1 mol/L). The active component obtained by ion exchange was first equilibrated with 0.02 mol/L of a Tris-HCl (pH 7.0) buffer containing 0.15 mol/L of NaCl, and an obtained sample was loaded onto a sephadex g25 gel chromatography column and eluted with the same buffer at a speed of 0.5 mL/min to obtain a purified enzyme solution.

The alkaline protease activity was determined by the short peptide substrate method in example 2; and a protein concentration was determined by a BCA protein concentration assay kit, the operation was performed according to the instructions, and a specific activity of the alkaline protease was value of a ratio of the enzyme activity (U/ml) to protein concentration (mg/ml). The specific activity of the wild-type recombinant strain was set as 1 and the specific activity of the mutant recombinant strain was expressed as a multiple of the specific activity of the wild-type recombinant strain. The results were as shown in the following table.

Specific Activity of Alkaline Protease

| Mutants | Specific activity (U/mg) | Specific activity multiple |
|---|---|---|
| Wild-type APR | 26.6 | 1 |
| APRM 1 | 614.5 | 23.1 |
| APRM 2 | 670.3 | 25.2 |
| APRM 3 | 598.5 | 22.5 |
| APRM 4 | 707.6 | 26.6 |
| APRM 5 | 696.9 | 26.2 |
| APRM 6 | 662.3 | 24.9 |
| APRM 7 | 673.0 | 25.3 |
| APRM 8 | 686.3 | 25.8 |

Determination of enzymatic properties: enzymatic properties of the wild type and mutants were determined. The results were shown in FIGS. 6A-6D. The wild-type alkaline protease had an optimal reaction temperature of 60° C. and an optimal reaction pH of 10. At a pH of 10 and 60° C., heat preservation was performed for 40 h, and residual enzyme activity was about 6%. At 60° C. and a pH of 11, heat preservation was performed for 70 h, and residual enzyme activity was about 21%. The enzymatic properties of the wild type and mutants were basically the same.

EXAMPLE 5

Construction of Highly Active Alkaline Protease Mutants in Other Bacillus

Figure 5:
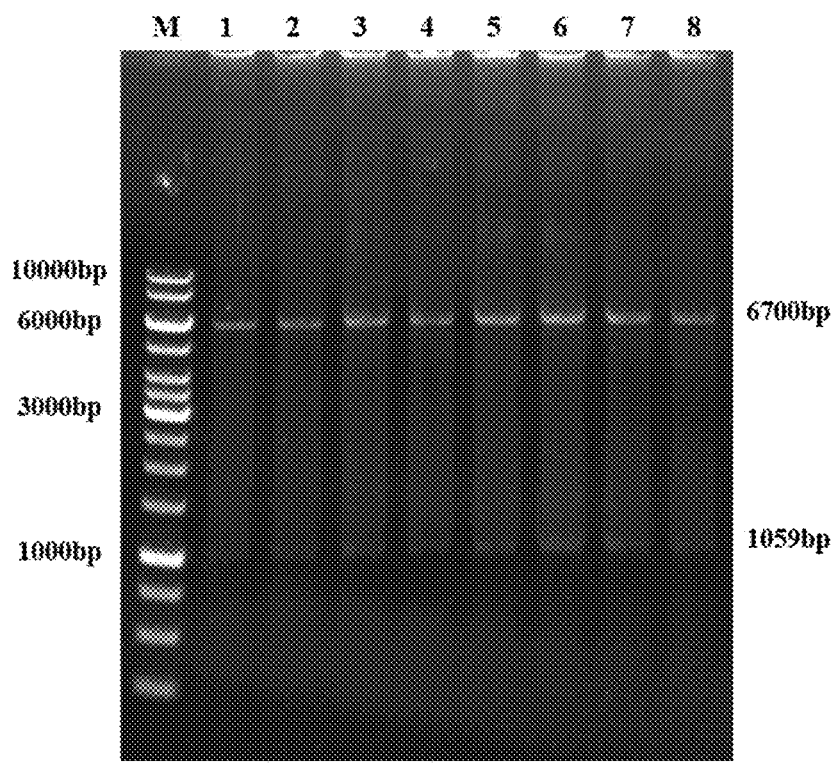
FIG. 5 is a verification diagram of digestion of a recombinant plasmid of pBSA43-aprmX in an example of the present disclosure,
where, M is DNA Marker and 1, 2, 3, 4, 5, 6, 7, and 8 show a double digestion map of recombinant plasmids pBSA43-aprm1, pBSA43-aprm2, pBSA43-aprm3, pBSA43-aprm4, pBSA43-aprm5, pBSA43-aprm6, pBSA43-aprm7 and pBSA43-aprm8 by BamHI and HindIII.
Figure 6A:
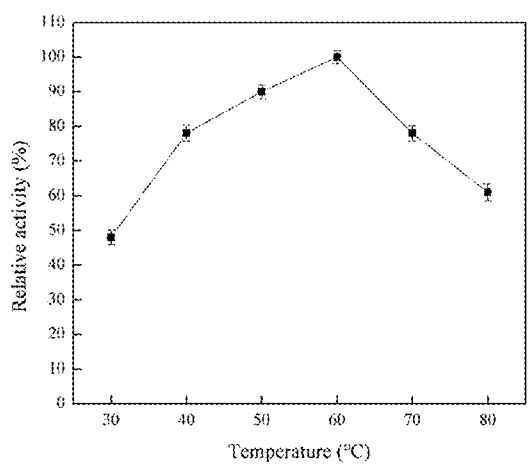
FIGS. 6A-6D show enzymatic properties of a wild-type alkaline protease APR in an example of the present disclosure,
where.
Figure 6B:
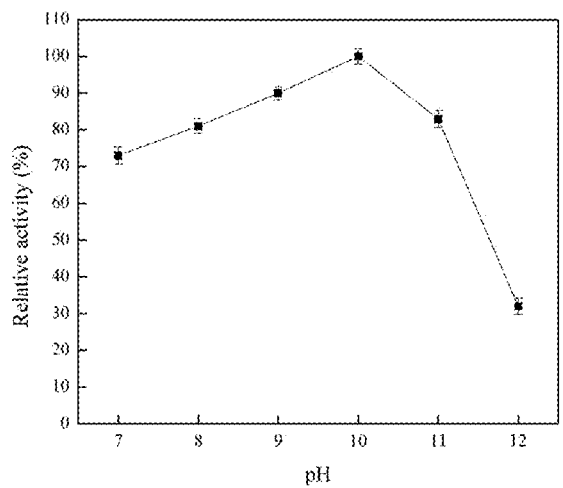
Figure 6C:
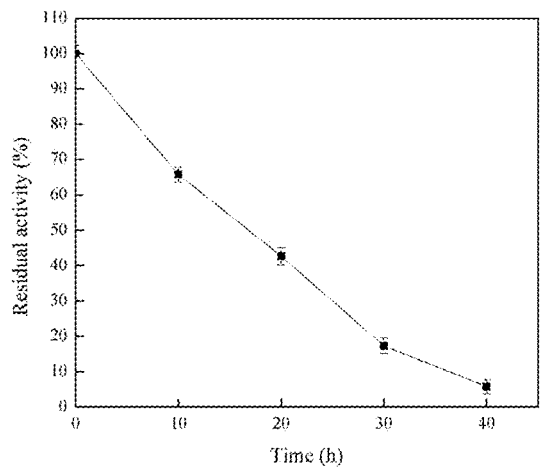
Figure 6D:
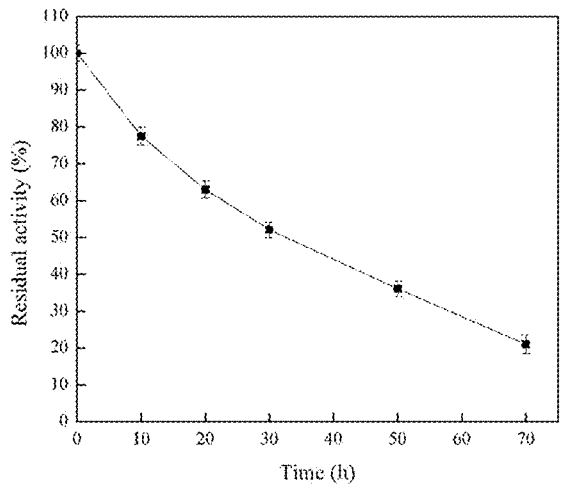

1 µL (50 ng/µL) of pBSA43-aprmX and pBSA43-apr recombinant plasmids were separately added into 50 µL of Bacillus amyloliquefaciens CGMCC No. 11218, Bacillus licheniformis TCCC11965, and Bacillus clausii CGMCC No. 12953 competent cells to be uniformly mixed, an obtained mixture was transferred to a pre-cooled electroporation cup (1 mm) and subjected to an ice bath for 1-1.5 min, and the treated mixture was electrically shocked once (25 µF, 200Ω, and 4.5-5.0 ms). Immediately after the electric shock, 1 mL of a resuscitation medium (LB+0.5 mol/L sorbitol+0.38 mol/L mannitol) was added. After cultured in shaking by a shaker at 37° C. for 3 h, a product after the resuscitation was spread on an LB plate containing kanamycin and cultured at 37° C. for 12-24 h. Positive transformants were picked and subjected to a double-enzyme digestion verification (FIG. 5). Recombinant strains of Bacillus amyloliquefaciens, Bacillus licheniformis, and Bacillus clausii expressing a mutant gene aprmX and a wild-type gene apr was obtained, and named CGMCC No. 11218/pBSA43-aprmX and CGMCC No. 11218/pBSA43-apr;

TCCC11965/pB SA43-aprmX and TCCC11965/pB SA43-apr; and CGMCC No. 12953/pBSA43-aprmX and CGMCC No. 12953/pBSA43-apr.

EXAMPLE 6

Expression and Preparation of Alkaline Protease Mutants in *Bacillus amyloliquefaciens* Recombinant Strain The *Bacillus amyloliquefaciens* mutant recombinant strain CGMCC No. 11218/pBSA43-aprmX and the wild-type recombinant strain CGMCC No. 11218/pBSA43-apr were separately inoculated in 5 mL of a LB liquid medium (containing 50 μg/mL of kanamycin) and cultured at 37° C. and 220 r/min overnight, the cultured strains were transferred to 50 mL of a fresh LB medium (containing 50 μg/mL of kanamycin) at an inoculum size of 2%, and the strains were continuously cultured at 37° C. and 220 r/min for 48 h.

A fermentation broth was centrifuged, a supernatant was taken, impure proteins were removed by salting out with ammonium sulfate at a saturation of 25%, and the saturation was increased to 65% to precipitate a target protein. After the precipitate was dissolved, dialysis was performed to remove salt, an active component obtained after salting out to desalt was dissolved with 0.02 mol/L of a Tris-HCl (pH 7.0) buffer, an obtained sample was loaded on a cellulose ion exchange chromatography column, unadsorbed protein was first eluted using the same buffer, and a target protein was collected by gradient elution with 0.02 mol/L of a Tris-HCl (pH 7.0) buffer containing different concentrations of NaCl (0-1 mol/L). The active component obtained by ion exchange was first equilibrated with 0.02 mol/L of a Tris-HCl (pH 7.0) buffer containing 0.15 mol/L of NaCl, an obtained sample was loaded onto a sephadex g25 gel chromatography column and eluted with the same buffer at a speed of 0.5 mL/min to obtain a purified enzyme solution, and the enzyme solution was freeze-dried to prepare purified alkaline protease powder. The prepared enzyme powder can be used in detergents, food, leather manufacturing, medicines and other industries.

EXAMPLE 7

Expression and Preparation of Alkaline Protease Mutants in *Bacillus licheniformis* Recombinant Strain The *Bacillus licheniformis* mutant recombinant strain TCCC11965/pBSA43-aprmX and the wild-type recombinant strain TCCC11965/pBSA43-apr were separately inoculated in 5 mL of a LB liquid medium (containing 50 μg/mL of kanamycin) and cultured at 37° C. and 220 r/min overnight, the cultured strains were transferred to 50 mL of a fresh LB medium (containing 50 μg/mL of kanamycin) at an inoculum size of 2%, and the strains were continuously cultured at 37° C. and 220 r/min for 48 h.

A fermentation broth was centrifuged, a supernatant was taken, impurity proteins were removed by salting out with ammonium sulfate at a saturation of 25%, and the saturation was increased to 65% to precipitate a target protein. After the precipitate was dissolved, dialysis was performed to remove salt, an active component obtained after salting out to desalt was dissolved with 0.02 mol/L of a Tris-HCl (pH 7.0) buffer, an obtained sample was loaded on a cellulose ion exchange chromatography column, unadsorbed protein was first eluted using the same buffer, and a target protein was collected by gradient elution with 0.02 mol/L of a Tris-HCl (pH 7.0) buffer containing different concentrations of NaCl (0-1 mol/L). The active component obtained by ion exchange was first equilibrated with 0.02 mol/L of a Tris-HCl (pH 7.0) buffer containing 0.15 mol/L of NaCl, an obtained sample was loaded onto a sephadex g25 gel chromatography column and eluted with the same buffer at a speed of 0.5 mL/min to obtain a purified enzyme solution, and the enzyme solution was freeze-dried to prepare purified alkaline protease powder. The prepared enzyme powder can be used in detergents, food, leather manufacturing, medicines and other industries.

EXAMPLE 8

Expression and Preparation of Alkaline Protease Mutants in *Bacillus clausii* Recombinant Strain The *Bacillus clausii* mutant recombinant strain CGMCC No. 12953/pBSA43-aprmX and the wild-type recombinant strain CGMCC No. 12953/pBSA43-apr were separately inoculated in 5 mL of a LB liquid medium (containing 50 μg/mL of kanamycin) and cultured at 37° C. and 220 r/min overnight, the cultured strains were transferred to 50 mL of a fresh LB medium (containing 50 μg/mL of kanamycin) at an inoculum size of 2%, and the strains were continuously cultured at 37° C. and 220 r/min for 48 h.

A fermentation broth was centrifuged, a supernatant was taken, impure proteins were removed by salting out with ammonium sulfate at a saturation of 25%, and the saturation was increased to 65% to precipitate a target protein. After the precipitate was dissolved, dialysis was performed to remove salt, an active component obtained after salting out to desalt was dissolved with 0.02 mol/L of a Tris-HCl (pH 7.0) buffer, an obtained sample was loaded on a cellulose ion exchange chromatography column, unadsorbed protein was first eluted using the same buffer, and a target protein was collected by gradient elution with 0.02 mol/L of a Tris-HCl (pH 7.0) buffer containing different concentrations of NaCl (0-1 mol/L). The active component obtained by ion exchange was first equilibrated with 0.02 mol/L of a Tris-HCl (pH 7.0) buffer containing 0.15 mol/L of NaCl, an obtained sample was loaded onto a sephadex g25 gel chromatography column and eluted with the same buffer at a speed of 0.5 mL/min to obtain a purified enzyme solution, and the enzyme solution was freeze-dried to prepare purified alkaline protease powder. The prepared enzyme powder can be used in detergents, food, leather manufacturing, medicines and other industries.

The above examples are merely illustrative of several implementations of the present disclosure, and the description thereof is more specific and detailed. However, these examples may not to be construed as a limitation to the scope of the patent. It should be noted that those of ordinary skill in the art can further make several variations, combinations and improvements without departing from the conception of the present disclosure. These variations, combinations and improvements all fall within the protection scope of the patent. Therefore, the protection scope of the patent shall be in accordance with the claims.

The invention claimed is:

1. An alkaline protease mutant comprising an amino acid sequence having at least 75% identity to SEQ ID NO: 6 and having any one of the following mutation combinations:

V11I/G23A/G25P/I35V/G95P/S99H/V145I/N212S/A267G,
V11L/G23A/G25P/I35V/G95P/S99H/V145I/N212S/A267G,
V11L/G23A/G25A/I35V/G95P/S99H/V145I/N212S/A267G,
V11I/G23A/G25A/I35V/G95P/S99H/V145I/N212S/A267G,
V11I/G23A/G25A/I35V/G95P/S99H/V145I/N212S/A267P,
V11L/G23A/G25A/I35V/G95P/S99H/V145I/N212S/A267P,
V11I/G23A/G25P/I35V/G95P/S99H/V145I/N212S/A267P, or
V11L/G23A/G25P/I35V/G95P/S99H/V145I/N212S/A267P.

2. An encoding gene comprising a nucleotide sequence encoding the alkaline protease mutant of claim 1.

3. The encoding gene according to claim 2, wherein the nucleotide sequence comprises any one of SEQ ID NOS: 7-14.

4. A recombinant vector comprising the encoding gene according to claim 2.

5. The recombinant vector according to claim 4, wherein the recombinant vector further comprises a *Bacillus* constitutive promoter and encodes a secretion signal peptide allowing for secretion expression of the alkaline protease mutant from a *Bacillus* host cell.

6. A recombinant strain comprising a host cell having the recombinant vector of claim 4.

7. The recombinant strain according to claim 6, where the host cell is *Bacillus subtilis, Bacillus amyloliquefaciens* or *Bacillus clausii*.

8. A method for producing an alkaline protease mutant, comprising:
culturing the recombinant strain of claim 6 to express the alkaline protease mutant.

9. A detergent or food comprising the alkaline protease mutant of claim 1.

* * * * *

```
                              SEQUENCE LISTING

Sequence total quantity: 14
SEQ ID NO: 1            moltype = DNA   length = 38
FEATURE                 Location/Qualifiers
misc_feature            1..38
                        note = The sequence is synthetized.
source                  1..38
                        mol_type = other DNA
                        organism = synthetic construct
SEQUENCE: 1
cgcggatccg ctgaagaagc aaaagaaaaa tatttaat                            38

SEQ ID NO: 2            moltype = DNA   length = 28
FEATURE                 Location/Qualifiers
misc_feature            1..28
                        note = The sequence is synthetized.
source                  1..28
                        mol_type = other DNA
                        organism = synthetic construct
SEQUENCE: 2
cccaagcttt tagcgtgttg ccgcttct                                       28

SEQ ID NO: 3            moltype = DNA   length = 1059
FEATURE                 Location/Qualifiers
source                  1..1059
                        mol_type = other DNA
                        organism = Bacillus clausii
SEQUENCE: 3
gctgaagaag caaaagaaaa atatttaatt ggctttaatg agcaggaagc tgtcagtgag    60
tttgtagaac aagtagaggc aaatgacgag gtcgccattc tctctgagga agaggaagtc   120
gaaattgaat tgcttcatga atttgaaacg attcctgttt tatccgttga gttaagccca   180
gaagatgtgg acgcgcttga actcgatcca gcgatttctt atattgaaga ggatgcagaa   240
gtaacgacaa tggcgcaatc agtgccatgg gaattagcc gtgtgcaagc cccagctgcc    300
cataaccgtg gattgacagg ttctggtgta aaagttgctg tcctcgatac aggtatttcc   360
actcatccaa acttaaatat tcgtgtggc gctagctttg taccagggga accatccact    420
caagatggga atgggcatgg cacgcatgtg gccgggacga ttgctgctt aaacaattcg    480
attggcgttc ttggcgtagc gccgagcgcg aactatacg ctgttaaagt attaggggcg    540
agcggttcag gttcggtcag ctcgattgcc caaggattgg aatgggcagg gaacaatggc   600
atgcacgttg ctaatttgag tttaggaagc ccttcgcaa gtgccacact tgagcaagct    660
gttaatagcg cgacttctag aggcgttctt gttgtagcgg catctgggaa ttcaggtgca   720
ggctcaatca gctatccggc ccgttatgcg aacgcaatgg cagtcggagc tactgaccaa   780
aacaacaacc gcgccagctt ttcacagtat ggcgcagggc ttgacattgt cgcaccaggt   840
gtaaacgtgc agagcacata cccaggttca acgtatgcca gcttaaacgg tacatccatg   900
gctactcctc atgttgcagg tgcagcagcc cttgttaaac aaaaagaaccc atcttggtcc   960
aatgtacaaa tccgcaatca tctaaagaat acggcaacga gcttaggaag cacgaacttg   1020
tatggaagcg gacttgtcaa tgcagaagcg gcaacacgc                          1059

SEQ ID NO: 4            moltype = AA    length = 353
FEATURE                 Location/Qualifiers
source                  1..353
                        mol_type = protein
                        organism = Bacillus clausii
SEQUENCE: 4
AEEAKEKYLI GFNEQEAVSE FVEQVEANDE VAILSEEEEV EIELLHEFET IPVLSVELSP    60
EDVDALELDP AISYIEEDAE VTTMAQSVPW GISRVQAPAA HNRGLTGSGV KVAVLDTGIS   120
THPDLNIRGG ASFVPGEPST QDGNGHGTHV AGTIAALNNS IGVLGVAPSA ELYAVKVLGA   180
SGSGSVSSIA QGLEWAGNNG MHVANLSLGS PSPSATLEQA VNSATSRGVL VVAASGNSGA   240
GSISYPARYA NAMAVGATDQ NNNRASFSQY GAGLDIVAPG VNVQSTYPGS TYASLNGTSM   300
ATPHVAGAAA LVKQKNPSWS NVQIRNHLKN TATSLGSTNL YGSGLVNAEA ATR          353

SEQ ID NO: 5            moltype = DNA   length = 807
FEATURE                 Location/Qualifiers
source                  1..807
                        mol_type = other DNA
                        organism = Bacillus clausii
SEQUENCE: 5
gcgcaatcag tgccatgggg aattagccgt gtgcaagccc cagctgccca taccgtgga    60
ttgacaggtt ctggtgtaaa agttgctgtc ctcgatacag gtatttccac tcatccagac   120
ttaaatattc gtgtggcgc tagctttgta ccaggggaac catccactca agatgggaat   180
gggcatggca cgcatgtggc cgggacgatt gctgctttaa acaattcgat tggcgttctt   240
ggcgtagcgc cgagcgcgga actatacgct gttaaagtat taggggcgag cggttcaggt   300
tcggtcagct cgattgccca aggattggaa tgggcaggga caatggcat gcacgttgct    360
aatttgagtt taggaagccc ttcgccaagt gccacacttg agcaagctgt taatagcgcg   420
acttctagag gcgttcttgt tgtagcggca tctgggaatt caggtgcagg ctcaatcagc   480
```

```
tatccggccc gttatgcgaa cgcaatggca gtcggagcta ctgaccaaaa caacaaccgc    540
gccagctttt cacagtatgg cgcagggctt gacattgtcg caccaggtgt aaacgtgcag    600
agcacatacc caggttcaac gtatgccagc ttaaacggta catcgatggc tactcctcat    660
gttgcaggtg cagcagccct tgttaaacaa aagaacccat cttggtccaa tgtacaaatc    720
cgcaatcatc taaagaatac ggcaacgagc ttaggaagca cgaacttgta tggaagcgga    780
cttgtcaatg cagaagcggc aacacgc                                        807

SEQ ID NO: 6            moltype = AA   length = 269
FEATURE                 Location/Qualifiers
source                  1..269
                        mol_type = protein
                        organism = Bacillus clausii
SEQUENCE: 6
AQSVPWGISR VQAPAAHNRG LTGSGVKVAV LDTGISTHPD LNIRGGASFV PGEPSTQDGN     60
GHGTHVAGTI AALNNSIGVL GVAPSAELYA VKVLGASGSG SVSSIAQGLE WAGNNGMHVA    120
NLSLGSPSPS ATLEQAVNSA TSRGVLVVAA SGNSGAGSIS YPARYANAMA VGATDQNNNR    180
ASFSQYGAGL DIVAPGVNVQ STYPGSTYAS LNGTSMATPH VAGAAALVKQ KNPSWSNVQI    240
RNHLKNTATS LGSTNLYGSG LVNAEAATR                                      269

SEQ ID NO: 7            moltype = DNA   length = 1059
FEATURE                 Location/Qualifiers
misc_feature            1..1059
                        note = The sequence is synthetized.
source                  1..1059
                        mol_type = other DNA
                        organism = synthetic construct
SEQUENCE: 7
gctgaagaag caaagaaaaa atatttaatt ggctttaatg agcaggaagc tgtcagtgag     60
tttgtagaac aagtagaggc aaatgacgag gtcgccattc tctctgagga agaggaagtc    120
gaaattgaat tgcttcatga atttgaaacg attcctgttt tatccgttga gttaagccca    180
gaagatgtgg acgcgcttga actcgatcca gcgatttctt atattgaaga ggatgcagaa    240
gtaacgacaa tggcgcaatc agtgccatgg ggaattagcc gtattcaagc cccagctgcc    300
cataaccgtg gattgacagc ttctcctgta aaagttgctg tcctcgatac aggtgtttcc    360
actcatccag acttaaatat tcgtggtggc gctagctttg taccagggga accatccact    420
caagatggga atgggcatgg cacgcatgtg gccgggacga ttgctgcttt aaacaattcg    480
attggcgttc ttggcgtagc gccgagcgcg gaactatacg ctgttaaagt attaccggcg    540
agcggtcacg gttcggtcag ctcgattgcc caaggattgg aatgggcagg aacaatggc    600
atgcacgttg ctaatttgag tttaggaagc ccttcgccaa gtgccacact tgagcaagct    660
gttaatagcg cgacttctag aggcattctt gttgtagcgg catctgggaa ttcaggtgca    720
ggctcaatca gctatccggc ccgttatgcg aacgcaatgg cagtcggagc tactgaccaa    780
aacaacaacc gcgccagctt ttcacagtat ggcgcagggc ttgacattgt cgcaccaggt    840
gtaaacgtgc agagcacata cccaggttca acgtatgcca gcttatccgg tacatcgatg    900
gctactcctc atgttgcagg tgcagcagcc cttgttaaac aaaagaaccc atcttggtcc    960
aatgtacaaa tccgcaatca tctaaagaat acggcaacga gcttaggaag cacgaacttg   1020
tatggaagcg gacttgtcaa tgcagaagcg ggaacacgc                          1059

SEQ ID NO: 8            moltype = DNA   length = 1059
FEATURE                 Location/Qualifiers
misc_feature            1..1059
                        note = The sequence is synthetized.
source                  1..1059
                        mol_type = other DNA
                        organism = synthetic construct
SEQUENCE: 8
gctgaagaag caaagaaaaa atatttaatt ggctttaatg agcaggaagc tgtcagtgag     60
tttgtagaac aagtagaggc aaatgacgag gtcgccattc tctctgagga agaggaagtc    120
gaaattgaat tgcttcatga atttgaaacg attcctgttt tatccgttga gttaagccca    180
gaagatgtgg acgcgcttga actcgatcca gcgatttctt atattgaaga ggatgcagaa    240
gtaacgacaa tggcgcaatc agtgccatgg ggaattagcc gttttcaagc cccagctgcc    300
cataaccgtg gattgacagc ttctcctgta aaagttgctg tcctcgatac aggtgtttcc    360
actcatccag acttaaatat tcgtggtggc gctagctttg taccagggga accatccact    420
caagatggga atgggcatgg cacgcatgtg gccgggacga ttgctgcttt aaacaattcg    480
attggcgttc ttggcgtagc gccgagcgcg gaactatacg ctgttaaagt attaccggcg    540
agcggtcacg gttcggtcag ctcgattgcc caaggattgg aatgggcagg aacaatggc    600
atgcacgttg ctaatttgag tttaggaagc ccttcgccaa gtgccacact tgagcaagct    660
gttaatagcg cgacttctag aggcattctt gttgtagcgg catctgggaa ttcaggtgca    720
ggctcaatca gctatccggc ccgttatgcg aacgcaatgg cagtcggagc tactgaccaa    780
aacaacaacc gcgccagctt ttcacagtat ggcgcagggc ttgacattgt cgcaccaggt    840
gtaaacgtgc agagcacata cccaggttca acgtatgcca gcttatccgg tacatcgatg    900
gctactcctc atgttgcagg tgcagcagcc cttgttaaac aaaagaaccc atcttggtcc    960
aatgtacaaa tccgcaatca tctaaagaat acggcaacga gcttaggaag cacgaacttg   1020
tatggaagcg gacttgtcaa tgcagaagcg ggaacacgc                          1059

SEQ ID NO: 9            moltype = DNA   length = 1059
FEATURE                 Location/Qualifiers
misc_feature            1..1059
                        note = The sequence is synthetized.
```

| source | 1..1059 |
| --- | --- |
| | mol_type = other DNA |
| | organism = synthetic construct |

SEQUENCE: 9

```
gctgaagaag caaagaaaa atatttaatt ggctttaatg agcaggaagc tgtcagtgag    60
tttgtagaac aagtagaggc aaatgacgag gtcgccattc tctctgagga agaggaagtc   120
gaaattgaat tgcttcatga atttgaaacg attcctgttt tatccgttga gttaagccca   180
gaagatgtgg acgcgcttga actcgatcca gcgatttctt atattgaaga ggatgcagaa   240
gtaacgacaa tggcgcaatc agtgccatgg gaattagcc gtttgcaagc cccagctgcc   300
cataaccgtg gattgacagc ttctgctgta aaagttgctg tcctcgatac aggtgtttcc   360
actcatccag acttaaatat tcgtggtggc gctagctttg taccagggga accatccact   420
caagatggga atgggcatgg cacgcatgtg gccgggacga ttgctgcttt aaacaattcg   480
attggcgttc ttggcgtagc gccgagcgcg gaactatacg ctgttaaagt attaccggcg   540
agcggtcacg gttcggtcag ctcgattgcc caaggattgg aatgggcagg gaacaatggc   600
atgcacgttg ctaatttgag tttaggaagc ccttcgccaa gtgccacact tgagcaagct   660
gttaatagcg cgacttctag aggcattctt gttgtagcgg catctgggaa ttcaggtgca   720
ggctcaatca gctatccggc ccgttatgcg aacgcaatgg cagtcggagc tactgaccaa   780
aacaacaacc gcgccagctt ttcacagtat ggcgcagggc ttgacattgt cgcaccaggt   840
gtaaacgtgc agagcacata cccaggttca acgtatgcca gcttatccgg tacatcgatg   900
gctactcctc atgttgcagg tgcagcagcc cttgttaaac aaaagaaccc atcttggtcc   960
aatgtacaaa tccgcaatca tctaaagaat acggcaacga gcttaggaag cacgaacttg  1020
tatgaagcg gacttgtcaa tgcagaagcg ggaacacgc                          1059
```

| SEQ ID NO: 10 | moltype = DNA length = 1059 |
| --- | --- |
| FEATURE | Location/Qualifiers |
| misc_feature | 1..1059 |
| | note = The sequence is synthetized. |
| source | 1..1059 |
| | mol_type = other DNA |
| | organism = synthetic construct |

SEQUENCE: 10

```
gctgaagaag caaagaaaa atatttaatt ggctttaatg agcaggaagc tgtcagtgag    60
tttgtagaac aagtagaggc aaatgacgag gtcgccattc tctctgagga agaggaagtc   120
gaaattgaat tgcttcatga atttgaaacg attcctgttt tatccgttga gttaagccca   180
gaagatgtgg acgcgcttga actcgatcca gcgatttctt atattgaaga ggatgcagaa   240
gtaacgacaa tggcgcaatc agtgccatgg gaattagcc gtattcaagc cccagctgcc   300
cataaccgtg gattgacagc ttctgctgta aaagttgctg tcctcgatac aggtgtttcc   360
actcatccag acttaaatat tcgtggtggc gctagctttg taccagggga accatccact   420
caagatggga atgggcatgg cacgcatgtg gccgggacga ttgctgcttt aaacaattcg   480
attggcgttc ttggcgtagc gccgagcgcg gaactatacg ctgttaaagt attaccggcg   540
agcggtcacg gttcggtcag ctcgattgcc caaggattgg aatgggcagg gaacaatggc   600
atgcacgttg ctaatttgag tttaggaagc ccttcgccaa gtgccacact tgagcaagct   660
gttaatagcg cgacttctag aggcattctt gttgtagcgg catctgggaa ttcaggtgca   720
ggctcaatca gctatccggc ccgttatgcg aacgcaatgg cagtcggagc tactgaccaa   780
aacaacaacc gcgccagctt ttcacagtat ggcgcagggc ttgacattgt cgcaccaggt   840
gtaaacgtgc agagcacata cccaggttca acgtatgcca gcttatccgg tacatcgatg   900
gctactcctc atgttgcagg tgcagcagcc cttgttaaac aaaagaaccc atcttggtcc   960
aatgtacaaa tccgcaatca tctaaagaat acggcaacga gcttaggaag cacgaacttg  1020
tatgaagcg gacttgtcaa tgcagaagcg ggaacacgc                          1059
```

| SEQ ID NO: 11 | moltype = DNA length = 1059 |
| --- | --- |
| FEATURE | Location/Qualifiers |
| misc_feature | 1..1059 |
| | note = The sequence is synthetized. |
| source | 1..1059 |
| | mol_type = other DNA |
| | organism = synthetic construct |

SEQUENCE: 11

```
gctgaagaag caaagaaaa atatttaatt ggctttaatg agcaggaagc tgtcagtgag    60
tttgtagaac aagtagaggc aaatgacgag gtcgccattc tctctgagga agaggaagtc   120
gaaattgaat tgcttcatga atttgaaacg attcctgttt tatccgttga gttaagccca   180
gaagatgtgg acgcgcttga actcgatcca gcgatttctt atattgaaga ggatgcagaa   240
gtaacgacaa tggcgcaatc agtgccatgg gaattagcc gtattcaagc cccagctgcc   300
cataaccgtg gattgacagc ttctgctgta aaagttgctg tcctcgatac aggtgtttcc   360
actcatccag acttaaatat tcgtggtggc gctagctttg taccagggga accatccact   420
caagatggga atgggcatgg cacgcatgtg gccgggacga ttgctgcttt aaacaattcg   480
attggcgttc ttggcgtagc gccgagcgcg gaactatacg ctgttaaagt attaccggcg   540
agcggtcacg gttcggtcag ctcgattgcc caaggattgg aatgggcagg gaacaatggc   600
atgcacgttg ctaatttgag tttaggaagc ccttcgccaa gtgccacact tgagcaagct   660
gttaatagcg cgacttctag aggcattctt gttgtagcgg catctgggaa ttcaggtgca   720
ggctcaatca gctatccggc ccgttatgcg aacgcaatgg cagtcggagc tactgaccaa   780
aacaacaacc gcgccagctt ttcacagtat ggcgcagggc ttgacattgt cgcaccaggt   840
gtaaacgtgc agagcacata cccaggttca acgtatgcca gcttatccgg tacatcgatg   900
gctactcctc atgttgcagg tgcagcagcc cttgttaaac aaaagaaccc atcttggtcc   960
aatgtacaaa tccgcaatca tctaaagaat acggcaacga gcttaggaag cacgaacttg  1020
tatgaagcg gacttgtcaa tgcagaagcg ccaacacgc                          1059
```

| SEQ ID NO: 12 | moltype = DNA  length = 1059 |
| --- | --- |
| FEATURE | Location/Qualifiers |
| misc_feature | 1..1059 |
| | note = The sequence is synthetized. |
| source | 1..1059 |
| | mol_type = other DNA |
| | organism = synthetic construct |

SEQUENCE: 12
```
gctgaagaag caaaagaaaa atatttaatt ggctttaatg agcaggaagc tgtcagtgag   60
tttgtagaac aagtagaggc aaatgacgag gtcgccattc tctctgagga agaggaagtc  120
gaaattgaat tgcttcatga atttgaaacg attcctgttt tatccgttga gttaagccca  180
gaagatgtgg acgcgcttga actcgatcca gcgatttctt atattgaaga ggatgcagaa  240
gtaacgacaa tggcgcaatc agtgccatgg ggaattagcc gtttgcaagc cccagctgcc  300
cataaccgtg gattgacagc ttctgctgta aaagttgctg tcctcgatac aggtgtttcc  360
actcatccag acttaaatat tcgtggtggc gctagctttg taccagggga accatccact  420
caagatggga atgggcatgg cacgcatgtg gccgggacga ttgctgcttt aaacaattcg  480
attggcgttc ttggcgtagc gccgagcgcg gaactatacg ctgttaaagt attaccggcg  540
agcggtcacg gttcggtcag ctcgattgcc caaggattgg aatgggcagg gaacaatggc  600
atgcacgttg ctaatttgag tttaggaagc ccttcgccaa gtgccacact tgagcaagct  660
gttaatagcg cgacttctag aggcattctt gttgtagcgg catctgggaa ttcaggtgca  720
ggctcaatca gctatccggc ccgttatgcg aacgcaatgg cagtcggagc tactgaccaa  780
aacaacaacc gcgccagctt ttcacagtat ggcgcagggc ttgacattgt cgcaccaggt  840
gtaaacgtgc agagcacata cccaggttca acgtatgcca gcttatccgg tacatcgatg  900
gctactcctc atgttgcagg tgcagcagcc cttgttaaac aaaagaaccc atcttggtcc  960
aatgtacaaa tccgcaatca tctaaagaat acggcaacga gcttaggaag cacgaacttg 1020
tatggaagcg gacttgtcaa tgcagaagcg ccaacacgc                          1059
```

| SEQ ID NO: 13 | moltype = DNA  length = 1059 |
| --- | --- |
| FEATURE | Location/Qualifiers |
| misc_feature | 1..1059 |
| | note = The sequence is synthetized. |
| source | 1..1059 |
| | mol_type = other DNA |
| | organism = synthetic construct |

SEQUENCE: 13
```
gctgaagaag caaaagaaaa atatttaatt ggctttaatg agcaggaagc tgtcagtgag   60
tttgtagaac aagtagaggc aaatgacgag gtcgccattc tctctgagga agaggaagtc  120
gaaattgaat tgcttcatga atttgaaacg attcctgttt tatccgttga gttaagccca  180
gaagatgtgg acgcgcttga actcgatcca gcgatttctt atattgaaga ggatgcagaa  240
gtaacgacaa tggcgcaatc agtgccatgg ggaattagcc gtattcaagc cccagctgcc  300
cataaccgtg gattgacagc ttctcctgta aaagttgctg tcctcgatac aggtgtttcc  360
actcatccag acttaaatat tcgtggtggc gctagctttg taccagggga accatccact  420
caagatggga atgggcatgg cacgcatgtg gccgggacga ttgctgcttt aaacaattcg  480
attggcgttc ttggcgtagc gccgagcgcg gaactatacg ctgttaaagt attaccggcg  540
agcggtcacg gttcggtcag ctcgattgcc caaggattgg aatgggcagg gaacaatggc  600
atgcacgttg ctaatttgag tttaggaagc ccttcgccaa gtgccacact tgagcaagct  660
gttaatagcg cgacttctag aggcattctt gttgtagcgg catctgggaa ttcaggtgca  720
ggctcaatca gctatccggc ccgttatgcg aacgcaatgg cagtcggagc tactgaccaa  780
aacaacaacc gcgccagctt ttcacagtat ggcgcagggc ttgacattgt cgcaccaggt  840
gtaaacgtgc agagcacata cccaggttca acgtatgcca gcttatccgg tacatcgatg  900
gctactcctc atgttgcagg tgcagcagcc cttgttaaac aaaagaaccc atcttggtcc  960
aatgtacaaa tccgcaatca tctaaagaat acggcaacga gcttaggaag cacgaacttg 1020
tatggaagcg gacttgtcaa tgcagaagcg ccaacacgc                          1059
```

| SEQ ID NO: 14 | moltype = DNA  length = 1059 |
| --- | --- |
| FEATURE | Location/Qualifiers |
| misc_feature | 1..1059 |
| | note = The sequence is synthetized. |
| source | 1..1059 |
| | mol_type = other DNA |
| | organism = synthetic construct |

SEQUENCE: 14
```
gctgaagaag caaaagaaaa atatttaatt ggctttaatg agcaggaagc tgtcagtgag   60
tttgtagaac aagtagaggc aaatgacgag gtcgccattc tctctgagga agaggaagtc  120
gaaattgaat tgcttcatga atttgaaacg attcctgttt tatccgttga gttaagccca  180
gaagatgtgg acgcgcttga actcgatcca gcgatttctt atattgaaga ggatgcagaa  240
gtaacgacaa tggcgcaatc agtgccatgg ggaattagcc gtttgcaagc cccagctgcc  300
cataaccgtg gattgacagc ttctcctgta aaagttgctg tcctcgatac aggtgtttcc  360
actcatccag acttaaatat tcgtggtggc gctagctttg taccagggga accatccact  420
caagatggga atgggcatgg cacgcatgtg gccgggacga ttgctgcttt aaacaattcg  480
attggcgttc ttggcgtagc gccgagcgcg gaactatacg ctgttaaagt attaccggcg  540
agcggtcacg gttcggtcag ctcgattgcc caaggattgg aatgggcagg gaacaatggc  600
atgcacgttg ctaatttgag tttaggaagc ccttcgccaa gtgccacact tgagcaagct  660
gttaatagcg cgacttctag aggcattctt gttgtagcgg catctgggaa ttcaggtgca  720
ggctcaatca gctatccggc ccgttatgcg aacgcaatgg cagtcggagc tactgaccaa  780
aacaacaacc gcgccagctt ttcacagtat ggcgcagggc ttgacattgt cgcaccaggt  840
gtaaacgtgc agagcacata cccaggttca acgtatgcca gcttatccgg tacatcgatg  900
```

-continued

```
gctactcctc atgttgcagg tgcagcagcc cttgttaaac aaaagaaccc atcttggtcc   960
aatgtacaaa tccgcaatca tctaaagaat acggcaacga gcttaggaag cacgaacttg  1020
tatggaagcg gacttgtcaa tgcagaagcg ccaacacgc                         1059
```